United States Patent
Schwaiger

(10) Patent No.: US 8,129,554 B2
(45) Date of Patent: Mar. 6, 2012

(54) METAL COMPLEXES

(75) Inventor: Jochen Schwaiger, Frankfurt (DE)

(73) Assignee: Merck Patent GmbH, Darmstadt (DE)

( * ) Notice: Subject to any disclaimer, the term of this patent is extended or adjusted under 35 U.S.C. 154(b) by 451 days.

(21) Appl. No.: 12/063,954

(22) PCT Filed: Jul. 24, 2006

(86) PCT No.: PCT/EP2006/007246
§ 371 (c)(1), (2), (4) Date: Jun. 30, 2008

(87) PCT Pub. No.: WO2007/019942
PCT Pub. Date: Feb. 22, 2007

(65) Prior Publication Data
US 2009/0118453 A1    May 7, 2009

(30) Foreign Application Priority Data
Aug. 18, 2005 (DE) .......... 10 2005 039 064

(51) Int. Cl.
*C07F 15/00* (2006.01)
*C08G 79/00* (2006.01)

(52) U.S. Cl. .......... 556/32; 549/3; 548/402; 546/4; 546/6; 528/9

(58) Field of Classification Search .......... 528/9; 546/4, 546/6; 548/402; 549/3; 556/32
See application file for complete search history.

(56) References Cited

U.S. PATENT DOCUMENTS
7,252,895 B2   8/2007   Seo et al.
2004/0241493 A1  12/2004  Inoue et al.

FOREIGN PATENT DOCUMENTS
EP   1211257 A2   6/2002
WO   WO-2004/048395 A1   6/2004

OTHER PUBLICATIONS

Uhlemann, "Zur Komplexbildung der 2-Picolylketone", *Journal für Praktische Chemie*, vol. 21, pp. 277-285 (1963).
El-Dissouky et al., "Metal Chelates of Heterocyclic Nitrogen containing Ketones, XIII. Cobalt(II), Nickel(II) and Palladium(II) Complexes of 2-Picolyl- and 2-Lutidyl-Methyl Ketones", *Transition Met. Chem.*, vol. 9, pp. 23-28 (1984).
El-Dissouky et al., "Metal Chelates of Heterocyclic Nitrogen-Containing Ketones. XIV. Metal Ion, Anion and Substituent Effects on the Enolization of Mono-Keto Compounds", *Inorganica Chimica Acta*, vol. 87, pp. 213-222 (1984).
Canty et al., "Synthetic and Structural Studies of Binuclear Organopalladium(II) Complexes Including a Bis(pyridin-2-yl)phenylmethyl Complex with Four- and Eight-Membered Palladocycle Rings, trans(N,N)-{Pd(μ-Py₂PhC-N,N'C')Cl}₂.½CH₂Cl₂.½Me₂CO", *Aust. J. Chem.*, vol. 41, pp. 651-665 (1988).
Fuchita et al., "Synthesis and Characterisation of the Six-Membered Cyclopalladated Complexes of 2-Benzylbenzothiazole", *Inorganica Chimica Acta*, vol. 239, pp. 125-132 (1995).
CAS Registry Number: 673476-36-3, 1 page (2005).
CAS Registry Number: 443151-86-8, 1 page (2005).

*Primary Examiner* — Porfirio Nazario Gonzalez
(74) *Attorney, Agent, or Firm* — Connolly Bove Lodge & Hutz LLP

(57) ABSTRACT

The present invention describes novel metal complexes. Compounds of this type can be employed as functional materials in a number of different applications which can be ascribed to the electronics industry in the broadest sense.

The compounds according to the invention are described by the formulae (1) and (1a).

18 Claims, No Drawings

METAL COMPLEXES

RELATED APPLICATIONS

This application is a national stage application (under 35 U.S.C. §371) of PCT/EP2006/007246, filed Jul. 24, 2006, which claims benefit of German application 10 2005 039 064.1, filed Aug. 18, 2005.

The present invention describes novel materials, the use thereof in organic electroluminescent elements, and displays based thereon.

Organometallic compounds, especially Ir and Pt compounds, are used as functional materials in a number of different applications which can be ascribed to the electronics industry in the broadest sense, for example in organic electroluminescent devices. The general structure of such devices is described, for example, in U.S. Pat. Nos. 4,539,507 and 5,151,629. A development which has taken place in recent years is the use of organometallic complexes which exhibit phosphorescence instead of fluorescence (M. A. Baldo et al., Appl. Phys. Lett. 1999, 75, 4-6). For quantum-mechanical reasons, an up to four-fold increase in energy and power efficiency is possible using organometallic compounds as phosphorescence emitters. Whether this development will be successful depends on whether corresponding device compositions are found which are also able to implement these advantages (triplet emission=phosphorescence compared with singlet emission=fluorescence) in the OLEDs. Essential conditions which may be mentioned here are, in particular, a long operating lifetime and high thermal stability of the complexes.

However, there are still considerable problems requiring urgent improve ment in OLEDs which exhibit triplet emission. This also applies, in particular, to the triplet emitter itself. Most of the complexes known in the literature contain ligands based on phenylpyridine or related structures, which coordinate to iridium or platinum (for example WO 02/068435, WO 04/026886 and EP1211257).

In practice, compounds of this type have some crucial weak points which require improvement:

1. A crucial deficiency is the low thermal stability of the compounds described above. Thus, for example, the homoleptic complex fac-tris(1-phenylisoquinoline-$C^2$,N)iridium(III)(Ir(piq)$_3$) cannot be sublimed without decomposition. Even under typical high-vacuum conditions (p<$10^{-7}$ mbar), considerable decomposition of this compound is observed, where, besides an iridium-containing ash which makes up about 30% by weight of the amount of Ir(piq)$_3$ employed, it is possible to detect the liberation of 1-phenylisoquinoline and other low-molecular-weight compounds. This thermal decomposition results in device characteristics which are virtually impossible to reproduce, adversely affecting the lifetime in particular. It is also necessary to have complexes with higher temperature stability available during purification of the metal complexes by sublimation since decomposition results in large losses of the complexes.
2. The operating lifetime is generally too short, which has hitherto also prevented the introduction of phosphorescent OLEDs into high-quality and long-life devices.
3. The complexes frequently have only low solubility in organic solvents, which makes efficient purification by recrystallisation or chromatography much more difficult or prevents it. This applies, in particular, to the purification of relatively large amounts, as required in display manufacture. The brominated complexes in particular, which can be used, for example, for the preparation of polymers, exhibit only low solubility and are therefore difficult to process during polymerisation.
4. The ligands for systems in accordance with the prior art, in particular for red-emitting complexes, are only accessible in complex, multistep processes.

There is therefore a demand for compounds which do not have the above-mentioned weak points, but are at least equal to the known metal complexes with respect to efficiency and emission colour.

US 2004/241493 describes a 5-membered chelate ring of an imine compound with iridium as white to whitish emitter. It is not apparent how other colours can be achieved using these complexes.

Surprisingly, it has been found that certain novel compounds which, instead of the five-membered chelate ring described above, use a six-membered chelate ring with an imine compound have improved properties as triplet emitters in OLEDs. For explanation, a five-membered iridium chelate ring and a six-membered iridium chelate ring are shown below, where D represents a coordinating atom, for example nitrogen, and C, as usual, stands for carbon:

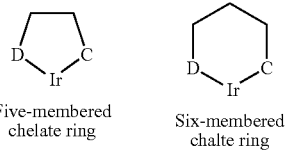

Five-membered chelate ring  Six-membered chalte ring

Metal complexes which contain six-membered and seven-membered chelate rings for use in OLEDs have in some cases already been described in the literature:

EP 1211257 describes metal complexes which contain a non-conjugated unit X, for example O, S, CR$_2$, etc., between the phenyl and pyridine rings of the ligand, giving six-membered chelate ring complexes with ligand systems which are not continuously conjugated. These complexes exhibit blue to orange-red emission, as revealed by the examples of the above-mentioned application, but are apparently not suitable for the generation of dark-red emission, which may possibly be due to the lack of conjugation of the ligand.

JP 2003/342284 describes similar six-membered chelate ring complexes in which the unit X is part of a larger ring system. In particular, X is the nitrogen of a carbazole system or a carbon in the 9-position of a fluorene. Systems with non-conjugated ligands are again formed here.

JP 2004/111193 describes conjugated and non-conjugated seven-membered chelate ring complexes.

The present invention relates to compounds of the formula (1)

$$M(L)_n(L')_m(L'')_o \qquad \text{Formula (1)}$$

containing a sub-structure $M(L)_n$ of the formula (2)

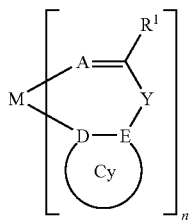

Formula (2)

where the following applies to the symbols and indices used:
M is a transition metal;
A is, identically or differently on each occurrence, NR or O;
D, for A=NR, is an sp²-hybridised carbon atom which bonds to M, and, for A=O, is a heteroatom having a non-bonding electron pair which coordinates to M;
E is, identically or differently on each occurrence, an sp²-hybridised carbon or nitrogen atom;
Cy is, identically or differently on each occurrence, a homo- or heterocycle which bonds to M via an sp²-hybridised carbon atom or a heteroatom having a non-bonding electron pair and to which one or more groups R are optionally bonded;
Y, for A=NR, is, identically or differently on each occurrence, $CR_2$, C(=O), C(=NR), C(=N—$NR_2$), C(=$CR_2$), $SiR_2$, O, S, S(=O), S(=O)$_2$, Se, NR, PR, P(=O)R, AsR, As(=O)R or BR and, for A=O, is equal to $CR^-$;
R, $R^1$ are, identically or differently on each occurrence, H, F, Cl, Br, I, CN, B(OH)$_2$, B(OR²)$_2$, NO$_2$, a straight-chain alkyl or alkoxy group having 1 to 40 C atoms or a branched or cyclic alkyl or alkoxy group having 3 to 40 C atoms, where one or more non-adjacent CH$_2$ groups may be replaced by —R²C=CR²—, —C≡C—, Si(R²)$_2$, Ge(R²)$_2$, Sn(R²)$_2$, —O—, —S—, —NR²—, —(C=O)—, —(C=NR²)—, —P=O(R²)— or —CONR²— and where one or more H atoms may be replaced by F, Cl, Br or I, or an aromatic or heteroaromatic ring system or an aryloxy or heteroaryloxy group having 5 to 40 C atoms, which may be substituted by one or more non-aromatic radicals R; R here may also form a further aliphatic or aromatic ring system with Cy;
$R^2$ is, identically or differently on each occurrence, H or an aliphatic or aromatic hydrocarbon radical having 1 to 20 C atoms, in which individual H atoms may also be replaced by F; two or more radicals $R^2$ here may also form a ring system with one another;
n is 1, 2 or 3;
the ligands L' and L" in formula (1) here are monoanionic, bidentate, chelating ligands; m and o are, identically or differently on each occurrence, 0, 1 or 2; n+m+o=2 here for metals with square-planar coordination, for example platinum and palladium, and n+m+o=3 for metals with octahedral coordination, for example iridium.

Hybridisation is taken to mean the linear combination of atomic orbitals. Thus, linear combination of one 2s and two 2p orbitals gives three equivalent sp² hybrid orbitals, which form an angle of 120° to one another. The remaining p orbital is capable of forming a π-bond, for example in an aromatic system.

For the purposes of the present invention, a $C_1$- to $C_{40}$-alkyl group, in which individual H atoms or CH$_2$ groups may also be substituted by the above-mentioned groups, is particularly preferably taken to mean the radicals methyl, ethyl, n-propyl, i-propyl, n-butyl, i-butyl, s-butyl, t-butyl, 2-methylbutyl, n-pentyl, s-pentyl, cyclopentyl, n-hexyl, cyclohexyl, n-heptyl, cycloheptyl, n-octyl, cyclooctyl, 2-ethylhexyl, trifluoromethyl, pentafluoroethyl, 2,2,2-trifluoroethyl, ethenyl, propenyl, butenyl, pentenyl, cyclopentenyl, hexenyl, cyclohexenyl, heptenyl, cycloheptenyl, octenyl, cyclo octenyl, ethynyl, propynyl, butynyl, pentynyl, hexynyl or octynyl. A $C_1$- to $C_{40}$-alkoxy group is particularly preferably taken to mean methoxy, ethoxy, n-propoxy, i-propoxy, n-butoxy, i-butoxy, s-butoxy, t-butoxy or 2-methylbutoxy. An aromatic or heteroaromatic system having 5-40 aromatic ring atoms, which may also in each case be substituted by the above-mentioned radicals $R^1$ and which may be linked to the aromatic or heteroaromatic ring via any desired positions, is taken to mean, in particular, groups derived from benzene, naphthalene, anthracene, phenanthrene, pyrene, chrysene, perylene, fluoranthene, tetracene, pentacene, benzopyrene, biphenyl, biphenylene, terphenyl, terphenylene, fluorene, spirobifluorene, truxene, isotruxene, dihydrophenanthrene, dihydropyrene, tetrahydropyrene, cis- or trans-indenofluorene, furan, benzofuran, isobenzofuran, dibenzofuran, thiophene, benzothiophene, isobenzothiophene, dibenzothiophene, pyrrole, indole, isoindole, carbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, benzopyridazine, pyrimidine, benzopyrimidine, quinoxaline, pyrazine, phenazine, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole.

Cy is preferably an aromatic or heteroaromatic system.

Preference is given to compounds of the formula (1) containing a sub-structure $M(L)_n$ of the formula (2a)

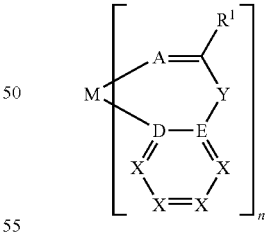

Formula (2a)

where M, A, Y, R, $R^1$, $R^2$, L', L", n, m and o have the same meaning as described above, and the following applies to the other symbols:
D, for A=NR, is an sp²-hybridised carbon atom which bonds to M, and, for A=O, is nitrogen or phosphorus, preferably nitrogen, which coordinates to M via the non-bonding electron pair;
X is, identically or differently on each occurrence, $CR^1$, N or P; or
(X—X) or (X=X) (i.e. two adjacent X) stands for $NR^1$, S or O; or (X—X) or (X═X) (i.e. two adjacent X) stands for $CR^1$, N or P if the symbol E stands for N; with the proviso that Cy represents a 5- or 6-membered ring;

E is, identically or differently on each occurrence, C or N, with the proviso that, if the symbol E stands for N, precisely one unit X—X (i.e. two adjacent X) in Cy is equal to $CR^1$, N or P.

A particularly preferred embodiment of the present invention comprises compounds of the formula (1a)

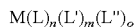      Formula (1a)

containing at least one sub-structure $M(L)_n$ of the formula (2b) and/or (2c)

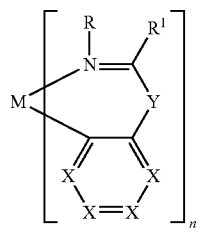      Formula (2b)

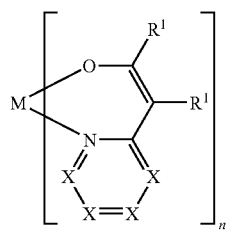      Formula (2c)

and optionally containing a sub-structure $M(L')_m$ of the formula (3)

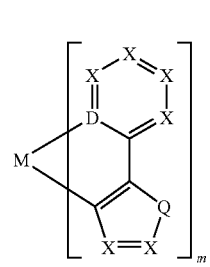      Formula (3)

where M, Y, D, R, $R^1$, $R^2$, L", n, m and o have the same meaning as described above, and furthermore:

X is, identically or differently on each occurrence, $CR^1$ or N; or (X—X) or (X═X) (i.e. two adjacent X) stands for $NR^1$, S or O; with the proviso that Cy represents a five- or six-membered ring;

Q is, identically or differently on each occurrence, —$CR^1$═$CR^1$—, —N═$CR^1$—, —N═N—, $NR^1$, O or S.

Preference is given to compounds of the formula (1) or formula (1a) in which the symbol Y, for A=NR, is, identically or differently, $CR_2$, C(═O), C(═$CR_2$), O, S, NR, PR, P(═O)R or BR and, for A=O, is $CR^-$. Particular preference is given to compounds of the formula (1) or formula (1a) in which the symbol Y, for A=NR, is, identically or differently, $CR_2$, O, S, NR or P(═O)R and, for A=O, is $CR^-$. Very particular preference is given to compounds of the formula (1) or formula (1a) in which the symbol Y, for A=NR, is equal to $CR_2$ or NR and, for A=O, is equal to $CR^-$.

Monoanionic, bidentate ligands L' according to the invention are 1,3-diketonates derived from 1,3-diketones, such as, for example, acetylacetone, benzoylacetone, 1,5-diphenylacetylacetone, bis(1,1,1-trifluoroacetyl)methane, 3-ketonates derived from 3-ketoesters, such as, for example, ethyl acetoacetate, carboxylates derived from aminocarboxylic acids, such as, for example, pyridine-2-carboxylic acid, quinoline-2-carboxylic acid, glycine, N,N-dimethylglycine, alanine, N,N-dimethylalanine, salicyliminates derived from salicylimines, such as, for example, methylsalicylimine, ethylsalicylimine, phenylsalicylimine, or borates of nitrogen-containing heterocyclic compounds, such as, for example, tetrakis(1-imidazolyl)borate and tetrakis(1-pyrazolyl)borate.

A particularly preferred embodiment of the invention relates to rigid systems of the formulae (2d) to (2f), in which the substituents R of Y form a five-membered ring or a six-membered ring with the ring Cy and/or the radical $R^1$

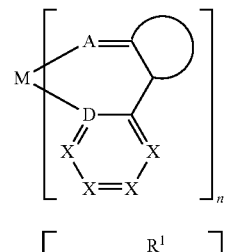      Formula (2d)

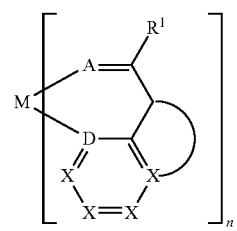      Formula (2e)

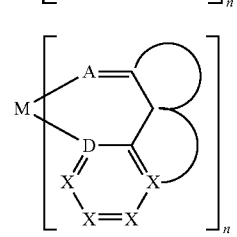      Formula (2f)

where the symbols and indices have the same meaning as described above.

Very particular preference is given to compounds of the formula (1) or formula (1a) containing a sub-structure M(L), of the formula (2g), of the formula (2h) or of the formula (2i)

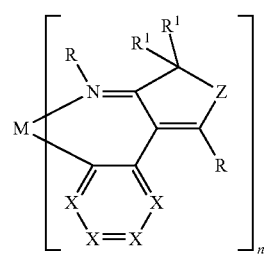      Formula (2g)

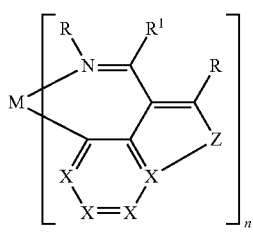

Formula (2h)

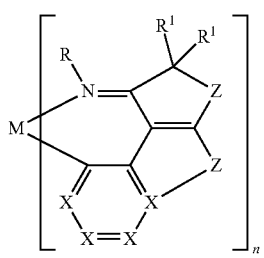

Formula (2i)

where M, X, R, $R^1$, $R^2$ and n have the same meaning as described above, and the following applies to the symbol Z:

Z is on each occurrence, identically or differently, a divalent group —C($R^1$)$_2$—, —C(=O)—, —C[=C($R^1$)$_2$]—, —C($R^1$)$_2$—C($R^1$)$_2$—, —C($R^1$)$_2$—C($R^1$)$_2$—C($R^1$)$_2$—, —C($R^1$)$_2$—O—C($R^1$)$_2$—, —C($R^1$)$_2$—N($R^1$)—, —C($R^1$)=C($R^1$)—, —C($R^1$)=N—, —O—, —S—, —N($R^1$)—, —P($R^1$)—, —P(=O)($R^1$)— or —B($R^1$)—.

In a further preferred embodiment of the invention, the ligand is built up and substituted in such a way that a five-membered chelate ring cannot form therefrom on coordination to a metal.

Preference is furthermore given to compounds of the formula (1) or formula (1a) in which the symbol M=Rh, Ir, Pd or Pt; particularly preferably, M=Ir or Pt, in particular Ir.

Preference is furthermore given to compounds of the formula (1) or formula (1a) in which the symbol n=2 or 3. Particular preference is given to compounds in which the symbol o=0. Very particular preference is given to compounds in which the symbol m=o=0. Particularly preferably, n=2 and m=o=0 for palladium and platinum complexes and n=3 and m=o=0 for rhodium and iridium complexes.

Preference is furthermore given to compounds of the formula (1) or formula (1a) in which the symbol X stands for $CR^1$.

Preference is given to the compounds of the formula (1) or formula (1a) according to the invention in which the symbol Z in formula (2g), (2h) or (2i) stands for a divalent group —C($R^1$)$_2$—, —C(=O)—, —C($R^1$)$_2$—C($R^1$)$_2$—, —C($R^1$)$_2$—N($R^1$)—, —C($R^1$)=C($R^1$)—, —C($R^1$)=N—, —O—, —S— or —N($R^1$)—. The symbol Z particularly preferably stands for —C($R^1$)$_2$—, —C($R^1$)$_2$—C($R^1$)$_2$—, —C($R^1$)=C($R^1$)—, —S— or —N($R^1$)—.

The corresponding ligands which produce sub-structures of the formula (2) or formulae (2a) to (2i), and also the ligands L' and L" can be prepared by common organochemical processes, as familiar to the person skilled in the art of organic synthesis. The precursors of the imine synthesis are frequently commercially available β-keto compounds, which react with amines with elimination of water to give imines. This synthesis is significantly simpler than the conventional ligand syntheses in accordance with the prior art.

The metal complexes according to the invention can in principle be prepared by various processes; however, the processes described below have proven to be particularly suitable.

The present invention therefore furthermore relates to a process for the preparation of the metal complexes according to the invention by reaction of the corresponding free ligands with metal alkoxides of the formula (4), with metal ketoketonates of the formula (5) or mono- or polycyclic metal halides of the formula (6), (7) or (8)

$$M(OR^2)_3$$ Formula (4)

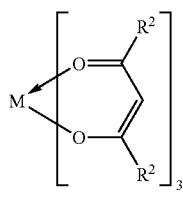

Formula (5)

$MHal_3$ Formula (6)

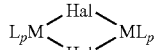

Formula (7)

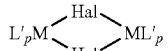

Formula (8)

where the symbols M and $R^2$ have the meanings indicated above, p=1 or 2, and Hal=F, Cl, Br or I.

It is likewise possible to use metal compounds, preferably rhodium and iridium compounds, which carry both alkoxide and/or halide and/or hydroxyl and also ketoketonate radicals. These compounds may also be charged. Corresponding iridium compounds which are particularly suitable as starting materials are disclosed in WO 04/085449.

The synthesis of the complexes is preferably carried out as described in WO 02/060910 and in WO 04/085449. Heteroleptic complexes can also be synthesised, for example, as described in WO 05/042548.

These processes enable the compounds of the formula (1) according to the invention to be obtained in high purity, preferably greater than 99% (determined by $^1$H-NMR and/or HPLC).

The synthetic methods explained here enable the preparation of, inter alia, structures (1) to (33) shown below for the compounds of the formula (1), which may also be substituted by substituents $R^1$. These substituents are in most cases not shown here for reasons of clarity.

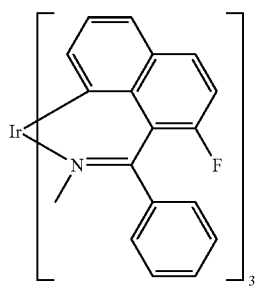

(1)

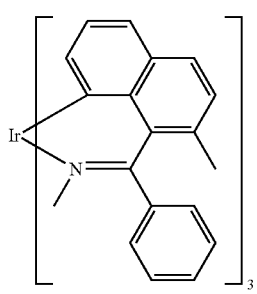 (2)
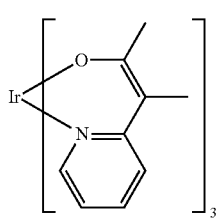 (3)
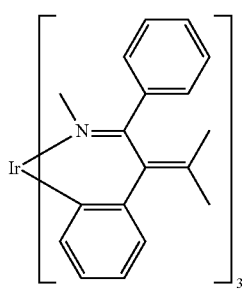 (4)
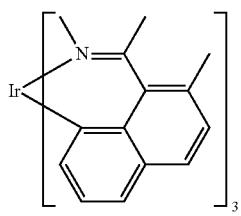 (5)
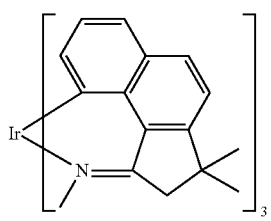 (6)
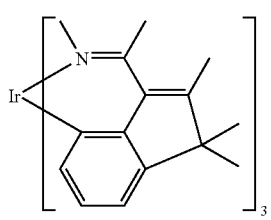 (7)
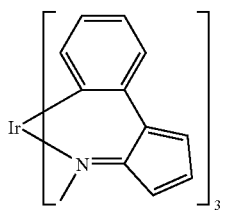 (8)
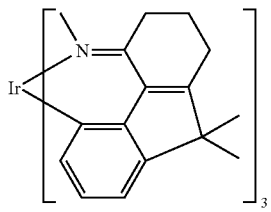 (9)
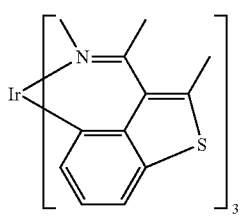 (10)
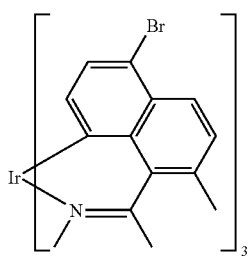 (11)
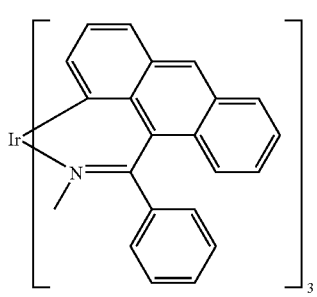 (12)
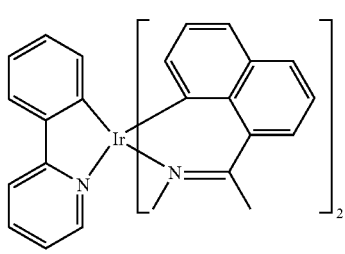 (13)

(14) 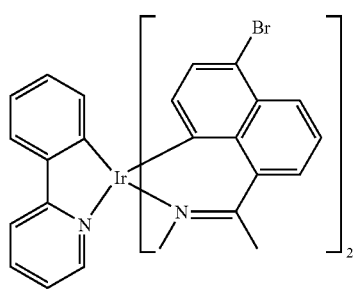
(15) 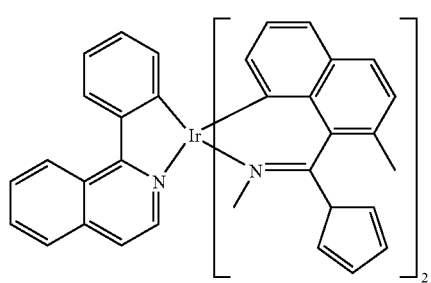
(16) 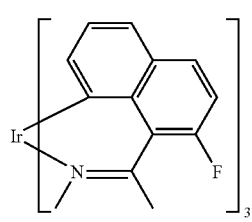
(17) 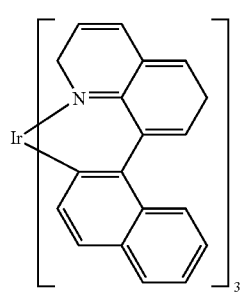
(18) 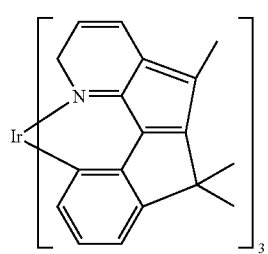
(19) 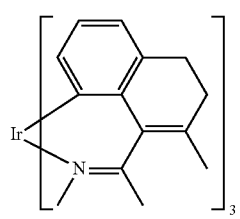
(20) 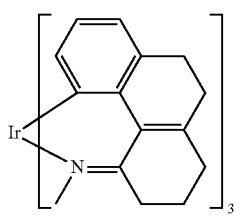
(21) 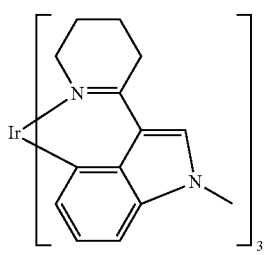
(22) 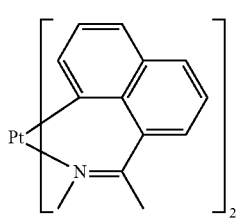
(23) 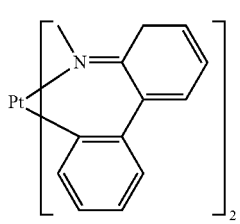
(24) 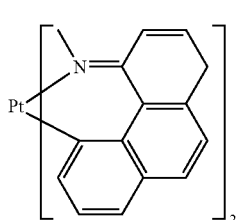
(25) 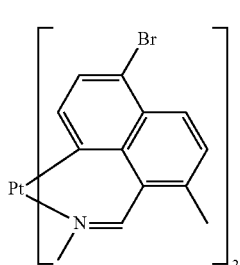
(26) 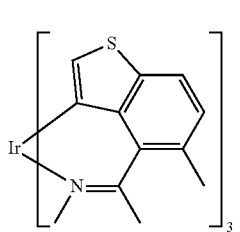

(27)

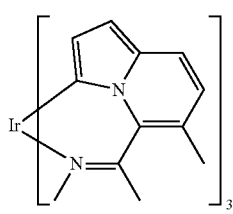

(28)

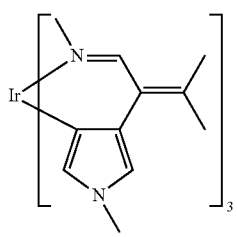

(29)

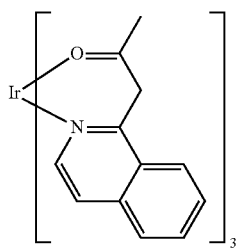

(30)

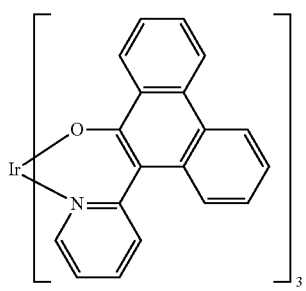

(31)

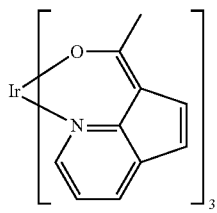

(32)

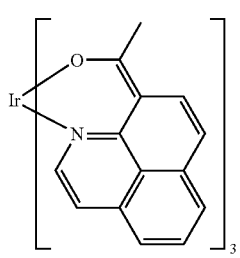

(33)

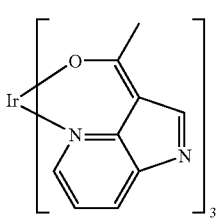

The compounds according to the invention described above, for example compounds (11), (14) and (25), can also be used as comonomers for the preparation of corresponding conjugated, partially conjugated or non-conjugated oligomers, polymers or dendrimers. The polymerisation here is preferably carried out via the bromine functionality. Further recurring units of the polymers are preferably selected from the group consisting of fluorenes (for example in accordance with EP 842208 or WO 00/22026), spirobifluorenes (for example in accordance with EP 707020 or EP 894107), dihydrophenanthrenes (for example in accordance with WO 05/014689), indenofluorenes (for example in accordance with WO 04/041901 and WO 04/113412), phenanthrenes (for example in accordance with WO 05/104264), para-phenylenes (for example in accordance with WO 92/18552), carbazoles (for example in accordance with WO 04/070772 or WO 04/113468), ketones (for example in accordance with WO 05/040302), silanes (for example in accordance with WO 05/111113), triarylamines or thiophenes (for example in accordance with EP 1028136), or also a plurality of different units thereof. They can either be incorporated here into the side chain or main chain of the polymer or may also represent branching points of the polymer chains (for example in accordance with WO 06/003000).

The invention thus furthermore relates to conjugated, partially conjugated or non-conjugated oligomers, polymers or dendrimers comprising one or more of the compounds of the formula (1) or formula (1a), where at least one of the radicals R or $R^1$ defined above, preferably $R^1$, represents a bond to the polymer or dendrimer, For units of the formula (1) or formula (1a), the same preferences as already described above apply in polymers and dendrimers.

The above-mentioned oligomers, polymers, copolymers and dendrimers are distinguished by good solubility in organic solvents and high efficiency and stability in organic electroluminescent devices.

The compounds of the formula (1) according to the invention, in particular those which are functionalised by halogens, may furthermore also be further functionalised by common reaction types and thus converted into extended compounds of the formula (1). An example which may be mentioned here is Suzuki functionalisation using arylboronic acids or Hartwig-Buchwald functionalisation using amines.

The compounds, oligomers, polymers, dendrimers or extended compounds of the formula (1) according to the invention are used as active components in electronic components, such as, for example, organic light-emitting diodes (OLEDs), organic integrated circuits (O-ICs), organic field-effect transistors (O-FETs), organic thin-film transistors (O-TFTs), organic field-quench devices (O-FQDs), organic light-emitting transistors (O-LETs), light-emitting electrochemical cells (LECs), organic solar cells (O—SCs) or organic laser diodes (O-lasers).

The present invention thus furthermore relates to the use of the compounds of the formula (1) according to the invention, the oligomers, polymers and dendrimers according to the invention and corresponding extended compounds of the formula (1) as active component in electronic components, in particular as emitting compound.

The invention furthermore relates to electronic components, in particular organic and polymeric light-emitting diodes (OLEDs, PLEDs), organic field-effect transistors (O-FETs), organic thin-film transistors (O-TFTs), organic integrated circuits (O-ICs), organic field-quench devices (O-FQDs), organic light-emitting transistors (O-LETs), light-emitting electrochemical cells (LECs), organic solar cells (O-SCs) and organic laser diodes (O-lasers), comprising one or more compounds of the formula (1) according to the invention, oligomers, polymers and dendrimers according to the invention and corresponding extended compounds of the formula (1), in particular as emitting compound.

The compounds according to the invention are preferably employed as emitting compounds in an emitting layer in an organic or polymeric light-emitting diode. In particular if they are low-molecular-weight compounds according to the invention, they are usually employed together with a matrix material. The matrix material here may either be of low molecular weight or oligomeric or polymeric.

Preferred matrix materials are those based on carbazoles, for example CBP (bis(carbazolyl)biphenyl), but also other materials comprising carbazole or carbazole derivatives, for example as described in WO 00/057676, EP 01/202358 and WO 02/074015. Preference is furthermore given to ketones and imines, as described, for example, in WO 04/093207, in particular those based on spirobifluorene, and phosphine oxides, phosphine selenides, phosphazenes, sulfoxides and sulfones, as described, for example, in WO 05/003253, in particular those based on spirobifluorene. Preference is furthermore given to silanes, polypodal metal complexes, for example as described in WO 04/081017, and oligophenylenes based on spirobifluorenes, for example as described in EP 676461 and WO 99/40051. Particularly preferred matrix materials are ketones, phosphine oxides, sulfoxides and sulfones. Very particular preference is given to ketones and phosphine oxides.

The compounds according to the invention have the following advantages over compounds in accordance with the prior art:

1. The compounds according to the invention are distinguished by high temperature stability. Thus, the low-molecular-weight compounds can be evaporated in a high vacuum without decomposition, and the oligomeric, dendritic and polymeric compounds are also very thermally stable, enabling the devices to be thermally treated without damage. This property is a basic prerequisite for reproducible production of OLEDs and, in particular, has a positive effect on the operating lifetime. Resource-conserving utilisation of compounds of these rare metals is thus furthermore possible since the complexes can be sub-limed with virtually no losses during purification.
2. The compounds according to the invention are distinguished by good solubility in organic solvents, which considerably simplifies their purification by common methods, such as recrystallisation or chromatography. The compounds can thus also be processed from solution by coating or printing techniques. This property is also advantageous during conventional processing by evaporation since the cleaning of the equipment or the shadow masks employed is thus considerably simplified.
3. The synthesis of the compounds according to the invention is distinguished by significantly simplified synthesis of the ligands in contrast to the complex systems in accordance with the prior art. Thus, these ligands are accessible in a few steps, in some cases even in one-step syntheses, from commercially available compounds, whereas complex syntheses are necessary for the ligand synthesis in accordance with the prior art, in particular for red-emitting systems.

EXAMPLES

The following syntheses are carried out under a protective-gas atmosphere, unless indicated otherwise. The starting materials can be purchased from ALDRICH or ABCR.

Example 1

Synthesis of Iridium Complex Ir1 a) Synthesis of Ligand L1

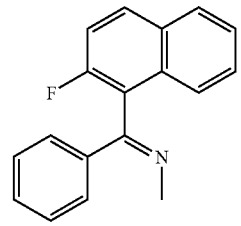

A solution of 25.1 g (0.272 mol) of phenylmagnesium bromide in 100 ml of dry THF is cooled to 0° C. A solution of 46.6 g (0.272 mol) of 1-cyano-2-fluoronaphthalene in 700 ml of dry THF is added to this solution over the course of 15 min. The reaction mixture is refluxed overnight and then cooled to −78° C. 187.5 ml (0.3 mol) of n-butyllithium (1.6M solution in hexane) are added to the mixture, and the mixture is stirred for 30 min. 18.7 ml (0.3 mol) of methyl iodide in 200 ml of dry THF are then added. The reaction mixture is warmed to room temperature and stirred for 2 h. 300 ml of water and 500 ml of diethyl ether are added, and the aqueous phase is separated off and extracted three times with diethyl ether. The combined organic phases are washed with saturated sodium chloride solution and dried over $MgSO_4$. After the solvent has been separated off, the product is purified by column chromatography on silica (heptane:EtOAc 65:35). Yield: 43.3 g (corresponds to 60.4% of theory).

b) Synthesis of the Chloro-Bridged Iridium Complex Dimer

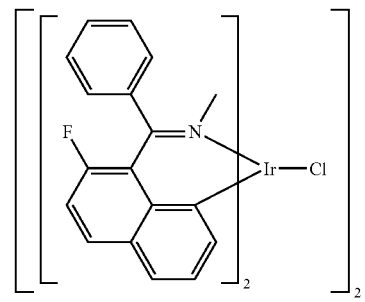

A degassed solution of 8.2 g (17 mmol) of $NaIr(acac)_2Cl_2$ and 21.8 g (83 mmol) of ligand L1 in 400 ml of triethylene glycol dimethyl ether is refluxed for 48 h. The suspension is cooled to room temperature, and the precipitate is filtered off with suction, washed with triethylene glycol dimethyl ether and ethanol and dried under reduced pressure. Yield: 9.7 g (73.6% of theory).

c) Synthesis of Complex Ir1

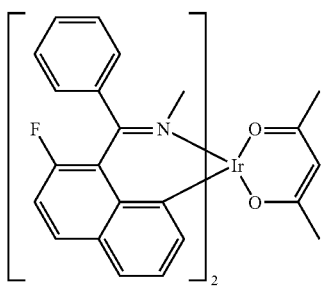

A degassed mixture of 2.4 g (1.73 mmol) of the complex from Example 1b), 0.43 g (4.29 mmol) of acetylacetone and 1.95 g (18.4 mmol) of sodium carbonate in 86 ml of methoxyethanol is refluxed for 16 h. The reaction mixture is cooled to room temperature, and the precipitate is filtered off with suction. The solid is washed with ethanol and hexane.

Example 2

Synthesis of Iridium Complex Ir2 a) Synthesis of the Precursor of Ligand L2

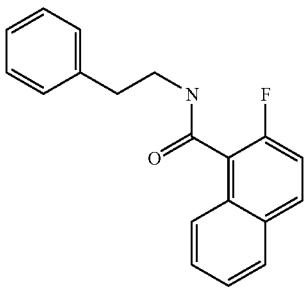

252 ml (2 mol) of phenylethylamine and 230 ml (2.24 mol) of triethylamine are dissolved in 500 ml of dichloromethane. 232 ml (2 mol) of 2-fluoronaphthyl chloride (dissolved in 200 ml of dichloromethane) are added dropwise to the solution at 0° C. at such a rate that the temperature does not rise above 40° C. The mixture is stirred overnight at room temperature. The precipitated white solid is dissolved in 3000 ml of dichloromethane. 700 ml of 2M NaOH are added. The mixture is then washed twice with 700 ml of dilute NaOH each time, three times with 700 ml of 1M HCl each time and twice with 700 ml of saturated NaHCO₃ solution each time. The organic phase is dried over MgSO₄, and the solvent is removed under reduced pressure. The solid is rinsed with a little dichloromethane and dried under reduced pressure. Yield: 475.6 g (81.1% of theory).

b) Synthesis of Ligand L2

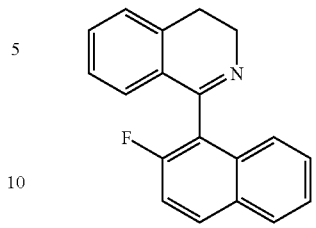

65.1 g (0.222 mol) of N-phenylethyl-2-fluoronaphthylamide from Example 2a) are dissolved in 375 ml of xylene at 90° C. 75.5 g (0.266 mol) of $P_2O_5$ are subsequently added in portions, and the reaction mixture is refluxed. 140 ml (0.658 mol) of $POCl_3$ are added dropwise to the hot reaction mixture, and the mixture is refluxed for a further 3 h. The hot reaction mixture is poured onto ice, and solid NaOH is carefully added until a pH of 12 has been reached. The precipitated phosphate is dissolved in 4 l of water. The phases are separated, and the aqueous phase is extracted three times with 300 ml of toluene each time. The combined organic phases are extracted three times with 300 ml of HCl each time (pH 1). 300 ml of toluene are added to the aqueous phase, and the pH is returned to 12 using solid NaOH. The aqueous phase is subsequently extracted three times with 150 ml of toluene each time. The combined organic phases are dried over $MgSO_4$, and the solvent is removed under reduced pressure. Yield: 89.7 g (97.1% of theory).

c) Synthesis of Complex Ir2

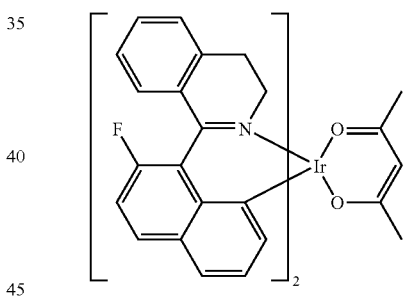

The synthesis of Ir2 is carried out analogously to the synthesis from Examples 1b) and 1c).

Examples 3-5

Production and Characterisation of Organic Electroluminescent Devices Comprising Compounds Ir1 and Ir2

Electroluminescent devices according to the invention can be produced as described, for example, in WO 05/003253. The results for two different OLEDs are compared here. The basic structure, the materials used, the degree of doping and their layer thicknesses are identical for better comparability. Only the dopant in the emission layer is varied. Example 3 describes a comparative standard in accordance with the prior art, in which the emission layer consists of the matrix material CBP and the guest material tris(phenylisoquinoline)iridium (Ir(piq)₃). An OLED comprising an emitter layer consisting of the matrix material CBP and the guest materials Ir1 and Ir2 is furthermore described (Examples 4 and 5). OLEDs having the following structure are produced analogously to the above-mentioned general process:

| | |
|---|---|
| PEDOT | 60 nm (spin-coated from water; PEDOT purchased from H.C. Starck, Goslar; poly-[3,4-ethylenedioxy-2,5-thiophene]) (HIL) |
| NaphDATA | 20 nm (vapour-deposited; NaphDATA purchased from SynTec; 4,4',4''-tris(N-1-naphthyl-N-phenylamino)-triphenylamine) (HTL) |
| S-TAD | 20 nm (vapour-deposited; S-TAD synthesised in accordance with WO 99/12888; 2,2',7,7'-tetrakis(diphenylamino)spirobifluorene) (HTL) |
| Emitter layer: | (EML) |
| CBP | 20 nm (vapour-deposited; CBP purchased from ALDRICH and purified further, finally sublimed twice; 4,4'-bis(N-carbazolyl)biphenyl) |
| Ir1 and Ir2 | (10% doping, vapour-deposited; synthesised in accordance with Examples 1 and 2) |
| OR: | |
| Ir(piq)$_3$ | (10% doping, vapour-deposited; synthesised in accordance with WO 03/0068526), comparative example |
| BCP | 10 nm (vapour-deposited; BCP purchased from ABCR, used as obtained; 2,9-dimethyl-4,7-diphenyl-1,10-phenanthroline) (HBL) |
| AlQ$_3$ | 10 nm (vapour-deposited; AlQ$_3$ purchased from SynTec; tris(quinolinato)aluminium(III)) (ETL) |
| LiF | 1 nm |
| Al | 100 nm. |

These still unoptimised OLEDs are characterised by standard methods; for this purpose, the electroluminescence spectra, the efficiency (measured in cd/A) as a function of the brightness, calculated from current/voltage/brightness characteristic lines (IUL characteristic lines), and the lifetime are determined.

OLEDs produced using the dopant Ir(piq)$_3$ typically give a maximum efficiency under the conditions described above of about 6.5 cd/A at colour coordinates of CIE: x=0.68, y=0.32. Voltages of 6.2 V are required for the reference luminance of 100 cd/m$^2$. The lifetime is about 250 h at an initial luminance of 500 cd/m$^2$ (see Table 1).

By contrast, OLEDs produced using dopants Ir1 and Ir2 according to the invention exhibit maximum efficiencies of 5.6 to 5.8 cd/A at colour coordinates (CIE) of x=0.70, y=0.30, with the requisite voltages for the reference luminance of 100 cd/m$^2$ being in the range from 5.3 to 5.4 V (see Table 1). The lifetime at an initial luminance of 500 cd/m$^2$ is, at 390 h to 510 h, better than that of the reference material Ir(piq)$_3$ (see Table 1).

TABLE 1

Device results with dopants according to the invention in CBP as matrix

| Example | EML | Max. eff. [cd/A] | Voltage [V] at 100 cd/m$^2$ | CIE (x, y) | Lifetime [h] (initial brightness 500 cd/m$^2$) |
|---|---|---|---|---|---|
| Example 3 (comparison) | CBP: 10% Ir(piq)$_3$ (30 nm) | 6.5 | 6.2 | 0.68/ 0.32 | 250 |
| Example 4 | CBP: 10% Ir1 (30 nm) | 5.8 | 5.4 | 0.70/ 0.30 | 390 |
| Example 5 | CBP: 10% Ir2 (30 nm) | 5.6 | 5.3 | 0.70/ 0.30 | 510 |

Examples 6 to 8

Further Device Examples with Dopants According to the Invention

Dopants Ir1 and Ir2 according to the invention and the comparative material Ir(piq)$_3$ in accordance with the prior art are tested in OLEDs comprising the matrix material M1 as described in WO 04/093207. OLEDs having the following structure are produced analogously to the process described in Examples 3-5:

| | |
|---|---|
| PEDOT | 80 nm (spin-coated from water; PEDOT purchased from H. C. Starck, Goslar; poly-[3,4-ethylenedioxy-2,5-thiophene]) (HIL) |
| NaphDATA | 20 nm (vapour-deposited; NaphDATA purchased from SynTec; 4,4',4''-tris(N-1-naphthyl-N-phenylamino)-triphenylamine) (HTL) |
| S-TAD | 20 nm (vapour-deposited; S-TAD synthesised in accordance with WO 99/12888; 2,2',7,7'-tetrakis(diphenylamino)spirobifluorene) (HTL) |
| Emitter layer: | (EML) |
| M1 | bis(9,9'-spirobifluoren-2-yl) ketone (vapour-deposited; synthesised in accordance with WO 2004/093207) Ir1 and Ir2 (10% doping, vapour-deposited; synthesised in accordance with Examples 1 and 2) |
| OR: | |
| Ir(piq)$_3$ | (10% doping, vapour-deposited; synthesised in accordance with WO 03/0068526) |
| HBM1 | 2,7-bis(4-biphenyl-1-yl)-2',7'-di-tert-butylspiro-9,9'-bifluorene (vapour-deposited; synthesised in accordance with WO 05/011334) |
| AlQ$_3$ | (vapour-deposited; AlQ$_3$ purchased from SynTec; tris(quinolinato)aluminium(III)) (ETL); |
| Ba/Al | 3 nm Ba, 150 nm Al on top. |

These still unoptimised OLEDs are characterised by standard methods; for this purpose, the electroluminescence spectra, the efficiency (measured in cd/A) as a function of the brightness, calculated from current/voltage/brightness characteristic lines (IUL characteristic lines), and the lifetime are determined The results obtained with these OLEDs are summarised in Table 2.

The matrix material M1, the hole-blocking material HBM1 and the comparative dopant Ir(piq)$_3$ are shown below for reasons of clarity:

TABLE 2

Device results with dopants according to the invention in M1 as matrix

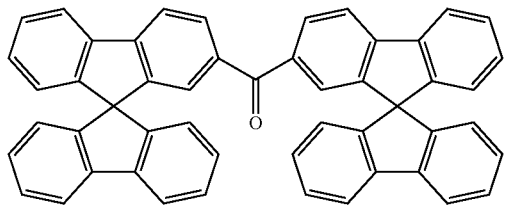

Bis(9,9'-spirobifluoren-2-yl) ketone
matrix material M1

TABLE 2-continued

Device results with dopants according to the invention in M1 as matrix

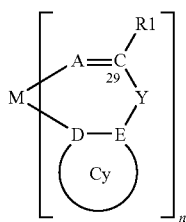

Ir(piq)₃

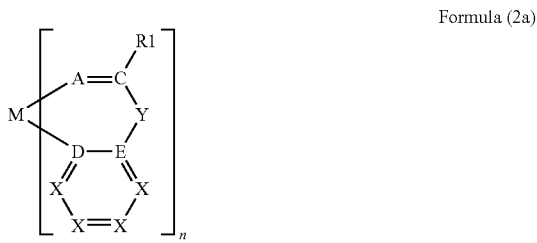

2,7-Bis(4-biphenyl-1-yl)-2',7'-di-tert-butylspiro-9,9'-bifluorene
HBM1

| Example | EML | Max. eff. [cd/A] | Voltage [V] at 100 cd/m² | CIE (x, y) | Lifetime [h] (initial brightness 1000 cd/m²) |
|---|---|---|---|---|---|
| Example 6 (comparison) | M1: 10% Ir(piq)₃ (30 nm) | 7.4 | 5.8 | 0.68/ 0.32 | 8300 |
| Example 7 | M1: 10% Ir1 (30 nm) | 6.5 | 4.9 | 0.70/ 0.30 | 8500 |
| Example 8 | M1: 10% Ir2 (30 nm) | 5.7 | 4.8 | 0.70/ 0.30 | 9000 |

As can be seen from Tables 1 and 2, the emitters according to the invention exhibit dark-red emission with better colour coordinates than the comparative material in accordance with the prior art and a lower operating voltage with an improved lifetime.

The invention claimed is:

1. A compound of formula (1)

$$M(L)_n(L')_m(L'')_o \qquad (1)$$

comprising
a substructure $M(L)_n$ of formula (2)

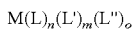

Formula (2)

wherein
M is a transition metal;
A is, identically or differently on each occurrence, NR or O;
D is an sp²-hybridised carbon atom which bonds to M
E is, identically or differently on each occurrence, an sp²-hybridised carbon or nitrogen atom;
Cy is, identically or differently on each occurrence, a homo- or heterocycle which bonds to M via an sp²-hybridised carbon atom and to which one or more groups R are optionally bonded;
Y is, identically or differently on each occurrence, $CR_2$, $C(=O)$, $C(=NR)$, $C(=N-NR_2)$, $C(=CR_2)$, $SiR_2$, O, S, $S(=O)$, $S(=O)_2$, Se, NR, PR, $P(=O)R$, AsR, $As(=O)R$, or ;
R and $R^1$
  are, identically or differently on each occurrence, H, F, Cl, Br, I, CN, $B(OH)_2$, $B(OR^2)_2$, $NO_2$; a straight-chain alkyl or alkoxy group having up to 40 C atoms, wherein one or more non-adjacent $CH_2$ groups are optionally replaced by $-R^2C=CR^2-$, $-C\equiv C-$, $Si(R^2)_2$, $Ge(R^2)_2$, $Sn(R^2)_2$, $-O-$, $-S-$, $-NR^2-$, $-(C=O)-$, $-(C=NR^2)-$, $-P=O(R^2)-$, or $-CONR^2-$, and wherein one or more H atoms are optionally replaced by F, Cl, Br, or I; a branched or cyclic alkyl or alkoxy group having up to 40 C atoms, wherein one or more non-adjacent $CH_2$ groups are optionally replaced by $-R^2C=CR^2-$, $-C\equiv C-$, $Si(R^2)_2$, $Ge(R^2)_2$, $Sn(R^2)_2$, $-O-$, $-S-$, $-NR^2-$, $-(C=O)-$, $-(C=NR^2)-$, $-P=O(R^2)-$, or $-CONR^2-$, and wherein one or more H atoms are optionally replaced by F, Cl, Br, or I; or an aromatic or heteroaromatic ring system or an aryloxy or heteroaryloxy group having 5 to 40 C atoms, optionally substituted by one or more non-aromatic radicals R; wherein R optionally defines a further aliphatic or aromatic ring system with Cy;
$R^2$ is, identically or differently on each occurrence, H or an aliphatic or aromatic hydrocarbon radical having up to 20 C atoms, wherein one or more H atoms are optionally replaced by F; and wherein two or more $R^2$ optionally define a ring system with one another;
n is 1, 2 or 3;
L' and L"
  are monoanionic, bidentate, chelating ligands;
m and o
  are, identically or differently on each occurrence, 0, 1 or 2; wherein
n+m+o=2 for metals with square-planar coordination and wherein n+m+o=3 for metals with octahedral coordination.

2. The compound of claim 1, wherein Cy is an aromatic or heteroaromatic system.

3. The compound of claim 1, wherein said substructure $M(L)_n$ is of formula (2a)

Formula (2a)

wherein
D is an sp²-hybridised carbon atom which bonds to M;
X is, identically or differently on each occurrence, $CR^1$, N or P; or is $NR^1$, S, or O, when (X—X) or (X=X) (i.e. two adjacent X); or is $CR^1$, N, or P, when (X—X) or (X=X) (i.e. two adjacent X) and E in the corresponding ring is N; with the proviso that Cy is a 5- or 6-membered ring;

E is, identically or differently on each occurrence, C or N, with the proviso that, if E is N, only one unit X—X (i.e. two adjacent X) in Cy is CR¹, N, or P.

4. The compound of claim 1, wherein said substructure M(L)$_n$ is of formula (2b)

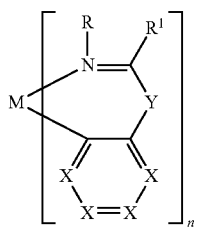

Formula (2b)

and optionally further comprises a sub-structure M(L')$_m$ of formula (3)

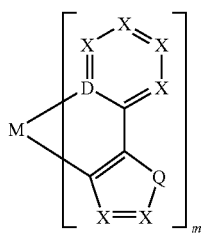

Formula (3)

wherein

X is, identically or differently on each occurrence, CR¹ or N; or is NR¹, S, or O, when (X—X) or (X=X) (i.e. two adjacent X); with the proviso that Cy is a 5- or 6-membered ring; and Q is, identically or differently on each occurrence, —CR¹=CR¹—, —N=N—, NR¹, O, or S.

5. The compound of claim 1, wherein said sub-structure M(L)$_n$ is of formulae (2g), (2h), or (2i)

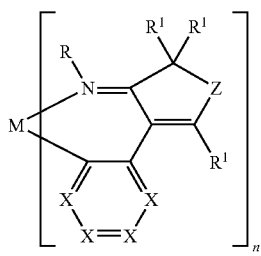

Formula (2g)

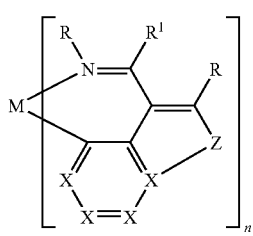

Formula (2h)

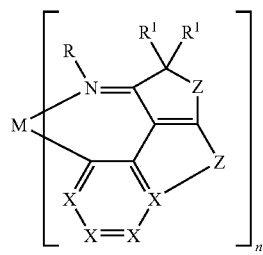

Formula (2i)

wherein

X is, identically or differently on each occurrence, CR¹, N or P; or is NR¹, S, or O, when (X—X) or (X=X) (i.e. two adjacent X); or is CR¹, N, or P, when (X—X) or (X=X) (i.e. two adjacent X) and E in the corresponding ring is N; with the proviso that Cy is a 5- or 6-membered ring;

Z is on each occurrence, identically or differently, a divalent group —C(R¹)$_2$-, —C(=O)—, —C[=C(R¹)$_2$]—, —C(R¹)$_2$—C(R¹)$_2$—, —C(R¹)$_2$—C(R¹)$_2$—C(R¹)$_2$—, —C(R¹)$_2$—O—C(R¹)$_2$—, —C(R¹)$_2$—N(R¹)—, —C(R¹)=C(R¹)—, —C(R¹)=N—, —O—, —S—, —N(R¹)—, —P(R¹)—, —P(=O)(R¹)—, or —B(R¹)—.

6. The compound of claim 1, wherein L″ is selected from the group consisting of 1,3-diketonates derived from 1,3-diketones, 3-ketonates derived from 3-ketoesters, carboxylates derived from arninocarboxylic acids, salicyliminates derived from salicylimines, and borates of nitrogen-containing heterocyclic compounds.

7. The compound of claim 1, wherein M is Rh, Ir, Pd, or Pt.

8. The compound of claim 1, wherein n is 2 or 3.

9. The compound of claim 1, wherein Y is, identically or differently, CR$_2$, C(=O), C(=NR), C(=CR$_2$), O, S, NR, or BR.

10. The compound of claim 3, wherein X is CR¹.

11. The compound of claim 1, wherein said compound is selected from structures (1) to (2), and (4) to (28).

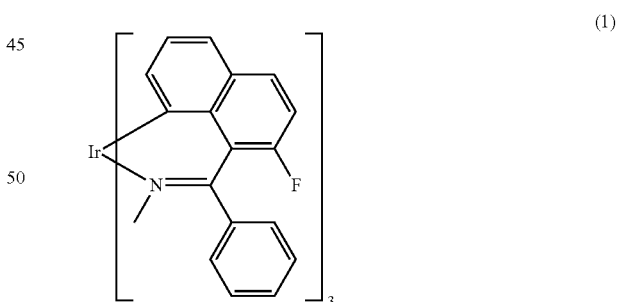

(1)

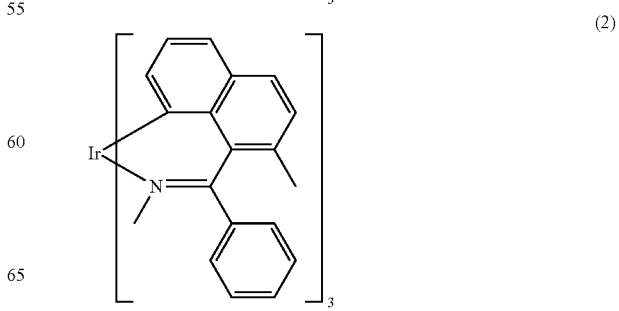

(2)

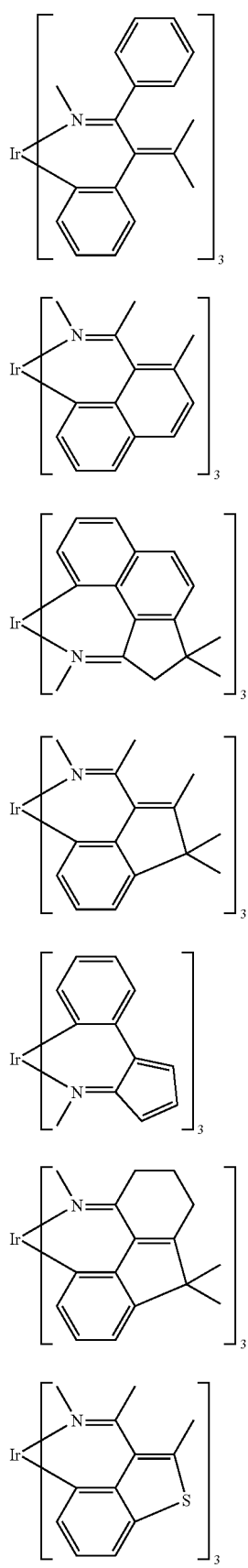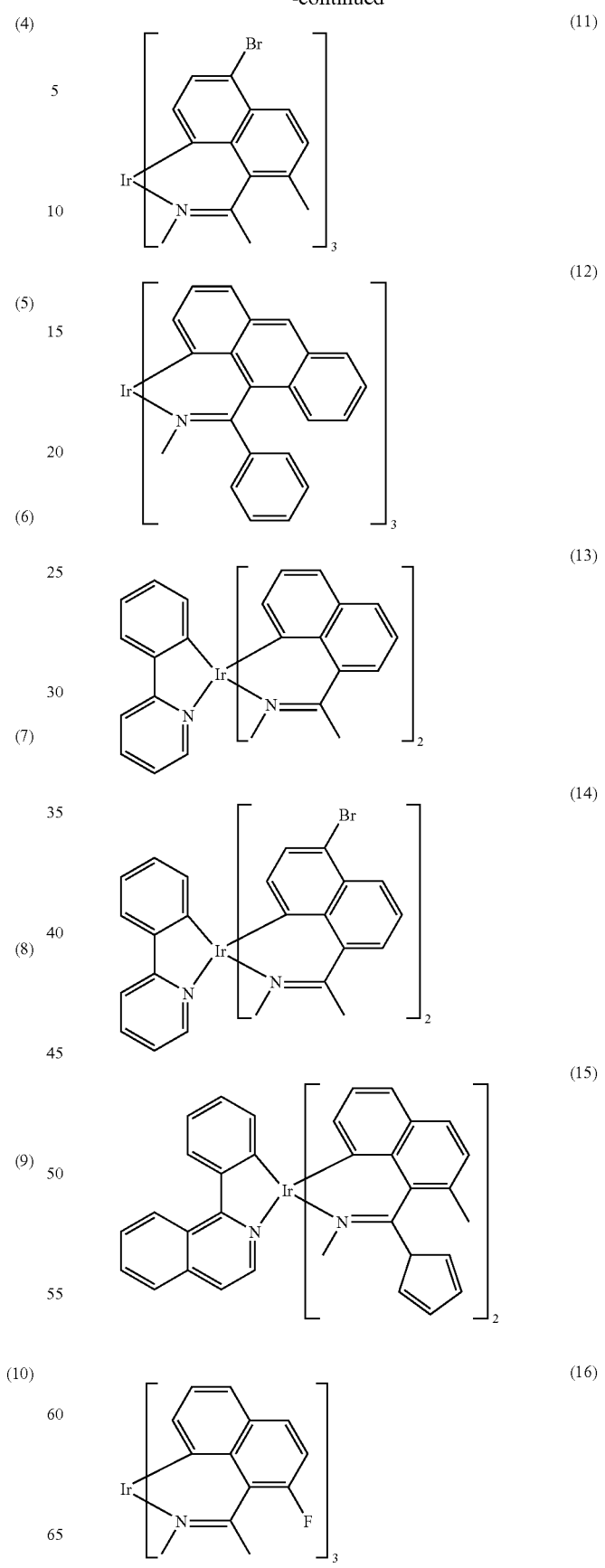

-continued
(17) 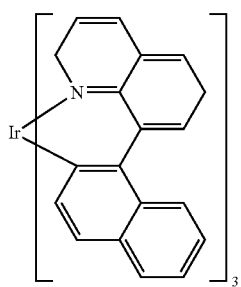
(18) 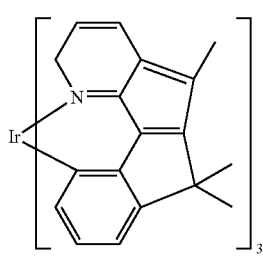
(19) 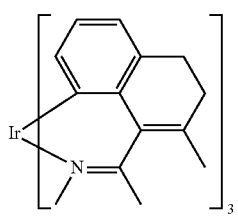
(20) 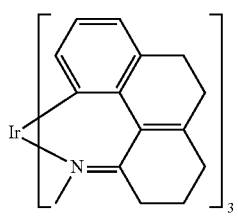
(21) 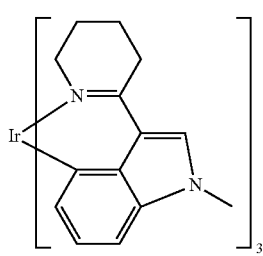
(22) 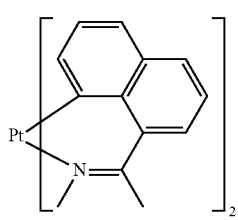
-continued
(23) 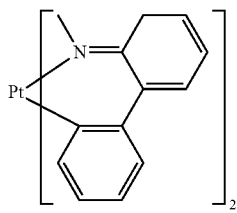
(24) 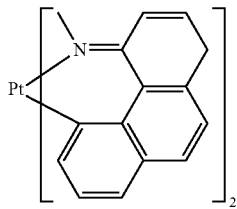
(25) 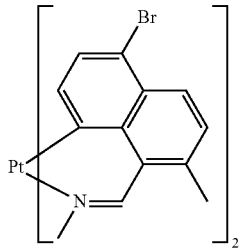
(26) 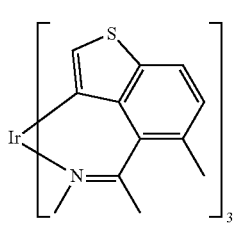
(27) 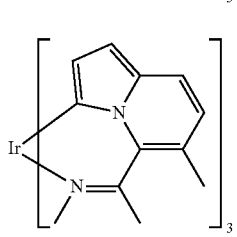
(28) 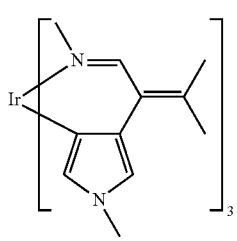
wherein said structures (1) to (2), and (4) to (28) are optionally substituted with $R^1$.
12. A process for preparing the compound of claim 1 comprising reacting the corresponding free ligands with metal alkoxides of formula (4), metal ketoketonates of formula (5), or mono- or polycyclic metal halides of formulae (6), (7), or (8)

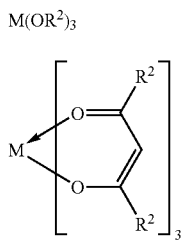 Formula (4)

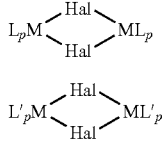 Formula (5)

$M(OR^2)_3$ ... (above)

MHal$_3$ Formula (6)

 Formula (7)

$L_pM\underset{Hal}{\overset{Hal}{<}}ML_p$ $L'_pM\underset{Hal}{\overset{Hal}{<}}ML'_p$ Formula (8)

wherein
p is 1 or 2; and
Hal is F, Cl, Br or I, or
with metal compounds which carry both alkoxide and/or halide and/or hydroxyl and also ketoketonate radicals.

13. A conjugated, partially conjugated, or non-conjugated oligomer, polymer, or dendrimer comprising one or more of the compounds of claim 1, wherein at least one of R and $R^1$ is a bond to said conjugated, partially conjugated, or non-conjugated oligomer, polymer, or dendrimer.

14. The conjugated, partially conjugated, or non-conjugated oligomer, polymer, or dendrimer of claim 13, further comprising additional recurring units selected from the group consisting of fluorenes, spirobifluorenes, dihydrophenanthrenes, indenofluorenes, phenanthrenes, para-phenylenes, carbazoles, ketones, silanes, triarylamines, thiophenes, and combinations thereof.

15. An emitting compound comprising one or more compounds of claim 1.

16. An electronic component comprising one or more compounds of claim 1.

17. The electronic component of claim 16, wherein said electronic component is selected from the group consisting of organic and polymeric light-emitting diodes, organic field-effect transistors, organic thin-film transistors, organic integrated circuits, organic field-quench devices, organic light-emitting transistors, light-emitting electrochemical cells, organic solar cells, and organic laser diodes.

18. An electronic component comprising one or more compounds of formula (1)

$M(L)_n(L')_m(L'')_o$ (1)

comprising
a substructure $M(L)_n$ of formula (2)

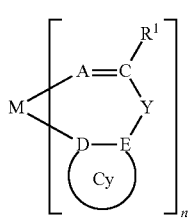 Formula (2)

wherein

M is a transition metal;

A is, identically or differently on each occurrence, NR or O;

D is an sp$^2$-hybridised carbon atom which bonds to M when A is NR and is a heteroatom having a non-bonding electron pair which coordinates to M when A is O;

E is, identically or differently on each occurrence, an sp$^2$-hybridised carbon or nitrogen atom;

Cy is, identically or differently on each occurrence, a homo- or heterocycle which bonds to M via an sp$^2$-hybridised carbon atom or a heteroatom having a non-bonding electron pair and to which one or more groups R are optionally bonded;

Y is, identically or differently on each occurrence, $CR_2$, C(=O), C(=NR),
C(=N-NR$_2$), C(=CR$_2$), SiR$_2$, O, S, S(=O), S(=O)$_2$, Se, NR, PR, P(=O)R, AsR,
As(=O)R, or BR when A is NR and is CR$^-$ when A is O;

R and $R^1$ are, identically or differently on each occurrence, H, F, Cl, Br, I, CN, B(OH)$_2$, B(OR$^2$)$_2$, NO$_2$; a straight-chain alkyl or alkoxy group having up to 40 C atoms, wherein one or more non-adjacent CH$_2$ groups are optionally replaced by
—R$^2$C=CR$^2$—, Si(R$^2$)$_2$, Ge(R$^2$)$_2$, Sn(R$^2$)$_2$, —O—, —S—, —(C=O)—, —(C=NR$^2$)—, —P=O(R$^2$)—, or —CONR$^2$—, and wherein one or more H atoms are optionally replaced by F, Cl, Br, or I; a branched or cyclic alkyl or alkoxy group having up to 40 C atoms, wherein one or more non-adjacent CH$_2$ groups are optionally replaced by —R$^2$C=CR$^2$—, Si(R$^2$)$_2$, Ge(R$^2$)$_2$, Sn(R$^2$)$_2$, —O—, —S—, —NR$^2$—, —(C=O)—, —(C=NR$^2$)—, —P=O(R$^2$)—, or —CONR$^2$-, and wherein one or more H atoms are optionally replaced by F, Cl, Br, or I; or an aromatic or heteroaromatic ring system or an aryloxy or heteroaryloxy group having 5 to 40 C atoms, optionally substituted by one or more non-aromatic radicals R; wherein R optionally defines a further aliphatic or aromatic ring system with Cy;

R$^2$ is, identically or differently on each occurrence, H or an aliphatic or aromatic hydrocarbon radical having up to 20 C atoms, wherein one or more H atoms are optionally replaced by F; and wherein two or more R$^2$ optionally define a ring system with one another;

n is 1, 2 or 3;

L' and L"

are monoanionic, bidentate, chelating ligands;

m and o are, identically or differently on each occurrence, 0, 1 or 2; wherein n+m+o=2 for metals with square-planar coordination and wherein n+m+o=3 for metals with octahedral coordination.

* * * * *